United States Patent
Kim et al.

(10) Patent No.: US 11,313,853 B2
(45) Date of Patent: Apr. 26, 2022

(54) METHOD OF PRODUCING TEST STRIP FOR COLORIMETRIC DETECTION OF CALCIUM CONTENT IN BODY FLUID USING CA-OCPC COMPLEX

(71) Applicant: CHUNGDO PHARM Co., Ltd, Chuncheon-si (KR)

(72) Inventors: Sung Jin Kim, Seoul (KR); Abeje Abebayehu Silte, Chuncheon-si (KR)

(73) Assignee: CHUNGDO PHARM Co., Ltd, Chuncheon-si (KR)

( * ) Notice: Subject to any disclaimer, the term of this patent is extended or adjusted under 35 U.S.C. 154(b) by 50 days.

(21) Appl. No.: 17/103,950

(22) Filed: Nov. 25, 2020

(65) Prior Publication Data

US 2022/0091106 A1 Mar. 24, 2022

(30) Foreign Application Priority Data

Sep. 23, 2020 (KR) .......................... 10-2020-0122768

(51) Int. Cl.
*G01N 33/52* (2006.01)
*G01N 21/78* (2006.01)
*G01N 21/77* (2006.01)

(52) U.S. Cl.
CPC .......... *G01N 33/523* (2013.01); *G01N 21/78* (2013.01); *G01N 2021/7759* (2013.01)

(58) Field of Classification Search
CPC ................. G01N 33/523; G01N 21/78; G01N 2021/7759
See application file for complete search history.

(56) References Cited

U.S. PATENT DOCUMENTS

2012/0275969 A1* 11/2012 Nakamura ........... G01N 33/526
422/400

FOREIGN PATENT DOCUMENTS

KR 10-2012-0135291 A 12/2012

* cited by examiner

*Primary Examiner* — Jennifer Wecker
*Assistant Examiner* — Kathryn Elizabeth Limbaugh
(74) *Attorney, Agent, or Firm* — Revolution IP, PLLC

(57) ABSTRACT

The present invention provides a method of producing a test strip for measuring a calcium concentration in a body fluid test sample obtained from a living body (human or animal) by a colormetric change, and a test strip for measuring a calcium concentration in a human or animal body fluid test strip by a colormetric change.

4 Claims, 1 Drawing Sheet

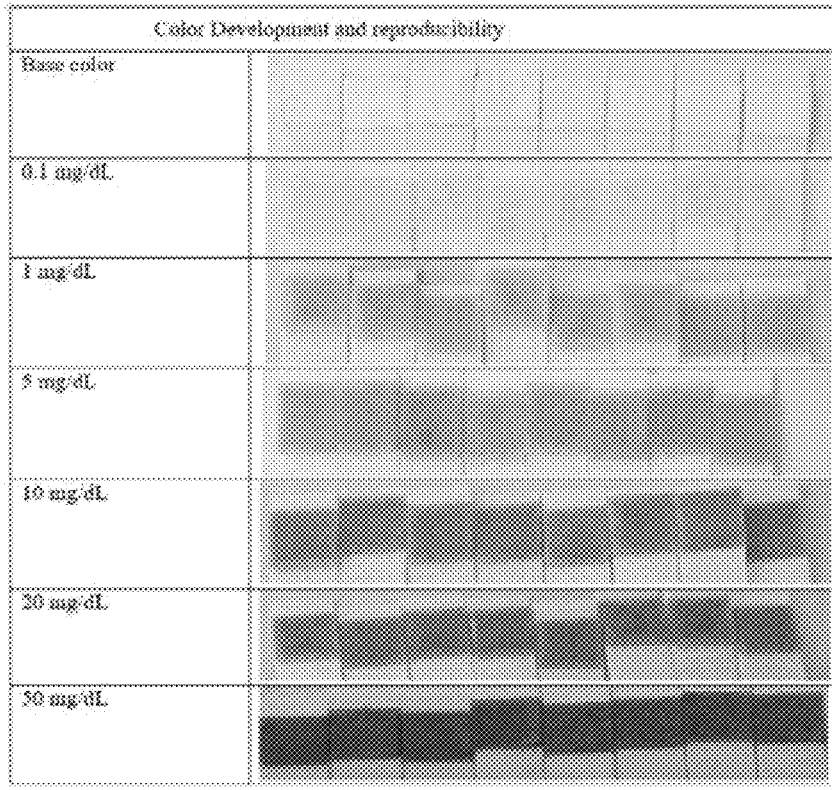

| Color Development and reproducibility | |
|---|---|
| Base color | |
| 0.1 mg/dL | |
| 1 mg/dL | |
| 5 mg/dL | |
| 10 mg/dL | |
| 20 mg/dL | |
| 30 mg/dL | |

METHOD OF PRODUCING TEST STRIP FOR COLORIMETRIC DETECTION OF CALCIUM CONTENT IN BODY FLUID USING CA-OCPC COMPLEX

CROSS-REFERENCE TO RELATED APPLICATION

This application claims priority to and the benefit of Korean Patent Application No. KR 10-2020-0122768 filed on Sep. 23, 2020, the disclosure of which is incorporated herein by reference in its entirety.

BACKGROUND

1. Field of the Invention

The present invention relates to a method of producing a test strip that is able to measure a calcium concentration in a fluid sample of a living body (a human or animal) by a colorimetric change.

2. Discussion of Related Art

Body fluids such as serum, urine and saliva include abundant biochemical markers excreted from the body. Accordingly, a human body fluid may be analyzed to measure the concentration of a specific metabolite or electrolyte, and a change in the concentration of a specific metabolite or electrolyte shows various medical conditions.

Calcium ions are very important for muscle contraction, neurotransmission, the formation of strong bones and teeth, blood clotting, the control of a heartbeat, or maintenance of intracellular balance. Like many metal ions, enzymes and hormones, the amount of calcium ions in blood is strictly regulated. A great change in blood calcium level leads to cancer, muscle problems and diseases.

In the case of a disease, a calcium concentration may be higher or lower than normal. A calcium change in blood may be due to parathyroid disease, a bone disease, incomplete calcium absorption in the intestines, a kidney disease, multiple myeloma and may other abnormalities. Accordingly, it is very important to quickly, easily and inexpensively measure the amount of calcium contained in a body fluid.

Calcium measurement is used in the diagnosis and treatment of parathyroid disease, various bone diseases and chronic kidney disease. While 99% or more of calcium is present in the bones and teeth of the body, clinically, calcium in the blood is most important. Bones release calcium when necessary to prevent a low calcium concentration, and absorb calcium to prevent an excessively high calcium concentration in the blood, and thus serve as a reservoir to maintain the relative homeostasis of calcium. The absorption and release of calcium into/from bones is regulated by the parathyroid hormone.

Hypocalcemia refers to a lower than normal calcium concentration in the blood. This may be caused by taking a diuretic, a therapeutic agent or a drug for treating a disease such as kidney function failure or hypotension. However, hypocalcemia is not generally caused by a lack of calcium in the diet. This is because the body extracts calcium from bones as needed to maintain a normal blood calcium level.

However, persistent dietary calcium deficiency may eventually lead to osteomalacia and osteoporosis, and suitable treatment is needed to reduce the risk of severe complications due to calcium deficiency. When calcium deficiency persists for a long time, it may lead to osteoporosis in which bones are weakened and the risk of fractures increases. Osteoporosis is characterized by decreased bone density and mass. Myeloid hip fractures cause significant morbidity and mortality in the elderly population.

As 60% of women aged 60 or more and 30% of males experienced osteoporotic fractures, osteoporosis has become more and more common in an aging population. Particularly, due to the fact that the incidence of osteoporosis is increasing in women, and if detected early, osteoporosis can be prevented by treatment, research on early detection and prediction of osteoporosis in postmenopausal women has become scientifically important.

Osteoporosis is certainly preventable, but only partially treatable. For this reason, for menopausal adults, the early detection of osteoporosis is important and may prevent exacerbation of the disease. There is a research result that many women have postmenopausal bone loss rates of 3% or more with a rate of up to 7% per year. In addition, there is a report that, in the majority of cases showing osteoporosis symptoms, 20 to 40% of the bone mineral content was already lost before diagnosis.

On the other hand, hypercalcemia refers to a higher than normal blood calcium level. Hypercalcemia is usually the result of a hyperactive parathyroid gland. Hypercalcemia most frequently occurs in breast cancer, lymphoma, prostate cancer, thyroid cancer, lung cancer, myeloma, or colon cancer. It may be due to the secretion of a parathyroid hormone-related peptide by a tumor, or may result from the release of calcium due to direct invasion of bones. Symptoms of hypercalcemia include anorexia, nausea, vomiting, constipation, abdominal pain, lethargy, depression, confusion, polyuria, and pain.

A highly specialized method such as bone densitometry helps in predicting the possibility of fractures, but is not generally performed due to a high cost. Therefore, when such a test is actually performed, most patients have already lost a considerable amount of bone minerals. As a result, such an expensive test does not actually help in diagnosing menopausal women who are prone to osteoporosis.

The successful detection of osteoporosis may be achieved by measuring a calcium concentration in serum or urine. Since it is commonly known that the amount of calcium in the urine is directly related to the bone loss rate of menopausal adults, the measurement of calcium in urine may act as an early indicator for rapid bone loss and may be used as an early diagnostic tool for predicting osteoporosis.

PRIOR ART DOCUMENT

Patent Document (Patent Document 0001) Korean Patent Application Publication No. 1020120135291 (Publication Date: Dec. 12, 2012), in which a reagent for measuring calcium and a measurement method using the reagent are disclosed.

SUMMARY OF THE INVENTION

The present invention is directed to providing a test strip which enables measurement of a calcium concentration in a human or animal body fluid test sample by a colorimetric change.

The present invention provides a method of producing a test strip for measuring a calcium concentration in a sample obtained from a living body, which includes: (a) immersing paper in a first reagent and drying it; and (b) immersing the dried paper in Step (a) in a second reagent and drying it, wherein the first reagent is prepared by adding and mixing o-cresolphthalein complexone (OPCP), 8-hydroxyquinoline, sodium dodecyl sulphate (SDS) and polyvinylpyrrolidone (PVP) in distilled water, and further adding an organic acid, and the second reagent is prepared by adding and mixing N-cyclohexyl-3-aminopropanesulfonic acid and N-methyl-D-glucamine in distilled water, and further adding Triton X-100 and triethylamine borate.

In the method of producing a test strip for measuring a calcium concentration in a sample obtained from a living body according to the present invention, the paper is preferably Whatman paper.

In the method of producing a test strip for measuring a calcium concentration in a sample obtained from a living body according to the present invention, the drying in Step (a) or drying in Step (b) is preferably performed at 55 to 65° C. for 10 to 20 minutes.

In the method of producing a test strip for measuring a calcium concentration in a sample obtained from a living body according to the present invention, the living body is preferably a human or animal.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 shows a test result for a calcium concentration previously adjusted to confirm the measurement efficiency of a test strip of the present invention.

DETAILED DESCRIPTION OF EXEMPLARY EMBODIMENTS

A recently known colorimetric method for measuring a calcium concentration is used for colorimetric measurement of calcium by chelating calcium with OCPC in the presence of an alkali buffer, and has been most widely used. However, since the pH of the prepared reagent itself is low, and it is difficult to control pH in many cases, a large measurement error is generated. In addition, the test strip produced according to the method results in false positive readings from the formation of a complex of magnesium and OCPC in a buffer solution with a pH 10.0 to 11.0. However, the method using this test strip includes instant color changes and provides the advantages of common calcium excretion testing, and thus is still widely used.

The present invention provides a test strip having a low error in the measurement of a calcium concentration by an OCPC method using two types of solutions indicated as a first reagent and a second reagent, by drying the first reagent and immersing a test strip in the second reagent. The present invention uses a sample obtained from a living body, which is preferably a human or animal. In addition, the sample obtained from a living body is preferably urine.

The method of producing a test strip according to the present invention is performed by two steps including immersing paper (preferably, Whatman paper) in a calcium dye reagent (first reagent) and drying it, and sequentially immersing the dried paper in a buffer solution (second reagent) and drying it.

A calcium dye reagent, which is the first reagent, is prepared by adding and mixing o-cresolphthalein complexone (OPCP), 8-hydroxyquinoline, sodium lauryl sulphate (SDS) and polyvinylpyrrolidone (PVP) in distilled water, and further adding citric acid.

The o-cresolphthalein complexone (OPCP) is a dye reacting with calcium to form a complex. Formula 1 below is a structural formula of o-cresolphthalein complexone.

[Formula 1]

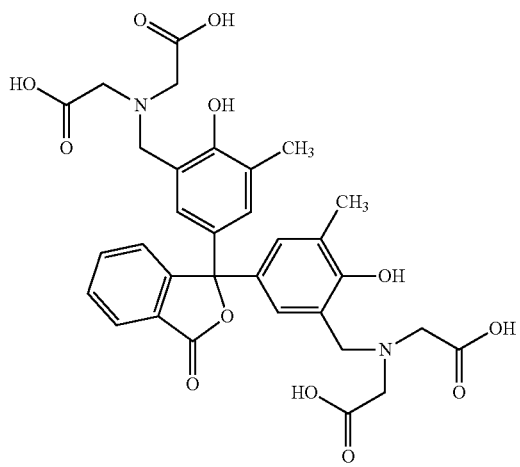

As shown below, OPCP reacts with calcium at pH 10 to 11, exhibiting a violet color.

[Scheme 1]

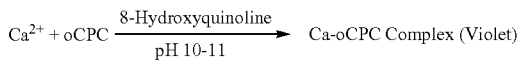

The 8-hydroxyquinoline is a component used to selectively mask magnesium causing false positives. In addition, 8-quinolinol sulfate or N-benzoyl-N-phenyl-hydroxylamine may also be used. The OCPC dye also reacts with magnesium within a pH range of 7 to 8, and as the pH increases, the reaction power is weakened. However, since the masking component can block interference caused by magnesium, it is recommended to use a component that selectively masks magnesium. By using a high pH (10 to 11) and a magnesium binder (8-hydroxyquinoline), magnesium acting as a source of interference in calcium measurement may be effectively removed.

The SDS is a non-ionic surfactant, and not subjected to hydrolysis by an acidic or alkali aqueous solution. These surfactant reagents including Triton-X-100 used among the second reagent improve the color and concentration of a dye with color changes. In addition, the level of chromatic dispersion throughout a reactive pad, the smoothness of the surface of a test strip and a color change rate are improved. In addition, it was revealed that these surfactants improve the brightness of a changing color and increase the absorption of a test strip.

The PVP is used as a stabilizer.

The organic acid is used as a pH buffer. The organic acid that is able to be used as a pH buffer may be selected from the group consisting of citric acid, malonic acid, phosphoric acid, malic acid, succinic acid, phthalic acid and glutamic acid. However, the organic acid is preferably citric acid.

Meanwhile, the buffer solution, which is a second solution (→second reagent), is prepared by adding and mixing N-cyclohexyl-3-aminopropanesulfonic acid and N-methyl-D-glucamine in distilled water, and further adding Triton X-100 and triethylamine borate.

The second reagent serves as a pH buffer for adjusting a pH to 10.0 to 11.0 in an environment for the reaction between calcium and OCPC. The buffer needs to maintain the pH of the sample within a pH range of 10 to 11, and at this high pH level, OCPC reacts with calcium ions, but does not highly react with magnesium.

A buffer suitable for a reagent composition may be selected from amino methyl propanol (AMP) or 3-(cyclohexyl amino)-1-propanesulfonic acid (CAPS), N-methyl-D-glucamine, a carbonate buffer and sodium borate, or a mixture thereof. However, it is preferable that N-cyclohexyl-3-aminopropanesulfonic acid and N-methyl-D-glucamine are used by adjusting triethyl amine borate, and N-cyclohexyl-3-aminopropanesulfonic acid and N-methyl-D-glucamine are mixed in a ratio of 9:1. It is important that the pH buffer does not react with calcium ions in the competition with a dye, and the pH buffer having the above components does not compete with the dye for calcium ions. Here, it is preferable that the concentration of the pH buffer is approximately 0.1 to 0.5M.

Meanwhile, the component Triton X-100 is a surfactant, whose role has been already described above.

Hereinafter, the present invention will be described in further detail with reference to the following examples and experimental examples. However, the scope of the present invention is not limited to only the following examples and experimental examples, and includes modification of equivalent technical ideas thereof Example 1: Production of Test Strip of the Present Invention According to the method of producing a test strip of the present invention, which is able to measure a calcium concentration in a biological sample, paper was sequentially immersed in a first reagent and a second reagent, and before transfer to the second reagent, characteristically, the paper was dried. That is, paper (Whatman paper) was immersed in a first reagent to be described below and then dried, and the dried paper was immersed in a second reagent and then dried, thereby producing a test strip of the present invention. Here, drying was performed at 60° C. for approximately 15 minutes.

① Preparation of First Reagent

Distilled water was used as a solvent, and 0.5 g of OPCP (component for measuring a calcium content), 5 g of 8-hydroxyquinoline (magnesium-selective masking reagent), 2.5 g of sodium lauryl sulphate (non-ionic surfactant) and 3.5 g of PVP (stabilizer) were mixed. Here, the pH was adjusted to 10 to 11 by adding citric acid.

② Preparation of Second Reagent

Distilled water was used as a solvent, and 3.3 g of N-cyclohexyl-3-aminopropanesulfonic acid (pH buffer) and 0.37 g of N-methyl-D-glucamine (pH buffer) were mixed. 0.2 g of Triton X-100 (surfactant) and 4 g of triethylamine borate (pH buffer) were added and mixed in this solution. In the final step, distilled water was added to make a final volume of 1 L.

The reagent test strip was formed from the above-mentioned first and second reagents. A pad is sensitive to calcium, and reacts when contacting a liquid obtained from a living body (urine, etc.) to have a color change according to a calcium concentration in the sample. Colorimetric assay may be performed by visually comparing a color change with a reference color chart, or using an analyzer that measures a concentration by calculating RGB values from a changed color to obtain an exact value. As the calcium concentration in the body fluid increases, the intensity of the expressed color may quantitatively indicate reproducibility, sensitivity and accuracy.

Experimental Example 1: Effectiveness Test for Test Strip of the Present Invention The effectiveness of the test strip of the present invention prepared as above was tested. FIG. 1 shows the test result with pre-adjusted calcium concentrations to confirm the effectiveness of measuring the test strip of the present invention. As shown in FIG. 1, it can be confirmed that a good colorimetric change occurs according to a calcium concentration.

The present invention provides a test strip which is able to measure a calcium concentration in a human or animal body fluid test sample by a colorimetric change, thereby easily and inexpensively monitoring a calcium excretion rate, and thus osteoporosis is able to be detected early.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of producing a test strip for measuring a calcium concentration in a sample obtained from a living body, comprising:
   (a) immersing paper in a first reagent and drying it; and
   (b) immersing the dried paper in Step (a) in a second reagent and drying it,
   wherein the first reagent is prepared by adding and mixing o-cresolphthalein complexone (OPCP), 8-hydroxyquinoline, sodium lauryl sulphate (SDS) and polyvinylpyrrolidone (PVP) in distilled water, and further adding an organic acid, and
   the second reagent is prepared by adding and mixing N-cyclohexyl-3-aminopropanesulfonic acid and N-methyl-D-glucamine in distilled water, and further adding Triton X-100 and triethylamine borate.

2. The method of claim 1, wherein the paper is Whatman paper.

3. The method of claim 1, wherein the drying in Step (a) or drying in Step (b) is performed at 55 to 65° C. for 10 to 20 minutes.

4. The method of claim 1, wherein the living body is a human or animal.

* * * * *